US010183400B2

(12) United States Patent
Trigui et al.

(10) Patent No.: US 10,183,400 B2
(45) Date of Patent: Jan. 22, 2019

(54) REUSABLE BUOYANCY MODULES FOR BUOYANCY CONTROL OF UNDERWATER VEHICLES

(71) Applicant: Saudi Arabian Oil Company, Dhahran (SA)

(72) Inventors: Hassane Trigui, Thuwal (SA); Ali Outa, Thuwal (SA); Sahejad Patel, Thuwal (SA); Fadl Abdellatif, Thuwal (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/675,714

(22) Filed: Aug. 12, 2017

(65) Prior Publication Data

US 2018/0079475 A1    Mar. 22, 2018

Related U.S. Application Data

(60) Provisional application No. 62/397,175, filed on Sep. 20, 2016.

(51) Int. Cl.
   *B63H 19/08*     (2006.01)
   *B25J 15/00*     (2006.01)
   (Continued)

(52) U.S. Cl.
   CPC ............. *B25J 15/0028* (2013.01); *B08B 1/00* (2013.01); *B08B 3/024* (2013.01); *B08B 9/023* (2013.01);
   (Continued)

(58) Field of Classification Search
   CPC .............................. B63H 19/08; B25J 15/0028
   See application file for complete search history.

(56) References Cited

U.S. PATENT DOCUMENTS

| 650,758 A | 5/1900 | Lake |
|---|---|---|
| 725,705 A | 4/1903 | Lake |

(Continued)

FOREIGN PATENT DOCUMENTS

| EP | 0071117 B1 | 5/1986 |
|---|---|---|
| JP | S 49-116789 A | 11/1974 |

(Continued)

OTHER PUBLICATIONS

Frey, C. et al., "Designing Modular Unmanned Landers to better observe life in the Deep Ocean," Sea Technology Magazine. pp. 3-6. Feb. 19, 2014.

*Primary Examiner* — Stephen P Avila
(74) *Attorney, Agent, or Firm* — Leason Ellis LLP

(57) ABSTRACT

A water environment robotic system and method has a buoyancy configuration which can be selectively altered. The system includes an underwater robotic vehicle and a buoyancy module that is configured to be selectively buoyantly engaged and buoyantly disengaged with the underwater robotic vehicle. A tether is connected to the buoyancy module and a motor is operatively connected to the tether and is configured to extend and retract the tether and buoyancy module. The tether can be extended and retracted to extend and retract the buoyancy module. Extending and retracting the buoyancy module can buoyantly engage or buoyantly disengage the buoyancy module with the underwater robotic vehicle according to the arrangement of the system. By engaging and disengaging the buoyancy module, the buoyancy of the underwater robot can be selectively altered.

12 Claims, 5 Drawing Sheets

Negatively Buoyant
"Crawling/landing"
Remote Controlled

(51) Int. Cl.
*B63G 8/00* (2006.01)
*F16H 19/08* (2006.01)
*B63G 8/14* (2006.01)
*B23K 31/12* (2006.01)
*B63G 8/42* (2006.01)
*G01B 17/02* (2006.01)
*G01N 29/22* (2006.01)
*G01N 29/04* (2006.01)
*B25J 9/00* (2006.01)
*B63C 11/42* (2006.01)
*E21B 41/04* (2006.01)
*B08B 1/00* (2006.01)
*B08B 3/02* (2006.01)
*B08B 9/023* (2006.01)
*B63C 11/52* (2006.01)
*F16H 35/18* (2006.01)
*F16L 1/26* (2006.01)
*F16L 55/00* (2006.01)
*B62D 57/00* (2006.01)

(52) U.S. Cl.
CPC ........... *B23K 31/125* (2013.01); *B25J 9/0009* (2013.01); *B25J 15/0009* (2013.01); *B63C 11/42* (2013.01); *B63C 11/52* (2013.01); *B63G 8/001* (2013.01); *B63G 8/14* (2013.01); *B63G 8/42* (2013.01); *E21B 41/04* (2013.01); *F16H 19/08* (2013.01); *F16H 35/18* (2013.01); *F16L 1/265* (2013.01); *G01B 17/02* (2013.01); *G01N 29/04* (2013.01); *G01N 29/225* (2013.01); *B62D 57/00* (2013.01); *B63G 8/00* (2013.01); *B63G 2008/002* (2013.01); *B63G 2008/005* (2013.01); *B63G 2008/008* (2013.01); *B63H 19/08* (2013.01); *F16H 2019/085* (2013.01); *F16L 55/00* (2013.01); *G01N 2291/0234* (2013.01); *G01N 2291/02854* (2013.01); *G01N 2291/2675* (2013.01)

(56) References Cited

U.S. PATENT DOCUMENTS

| | | | |
|---|---|---|---|
| 1,195,317 | A | 8/1916 | Woods |
| 3,393,524 | A | 7/1968 | Terrell |
| 3,402,687 | A | 9/1968 | Tsuji |
| 3,500,648 | A | 3/1970 | Daniell |
| 3,550,385 | A | 12/1970 | Lowd et al. |
| 3,631,550 | A | 1/1972 | Bullen |
| 3,675,607 | A * | 7/1972 | Dorschel ............... B63C 11/36 114/314 |
| 4,096,598 | A | 6/1978 | Mason |
| 4,109,601 | A | 8/1978 | Ronnevig |
| 4,231,171 | A | 11/1980 | Balligand et al. |
| 4,289,425 | A | 9/1981 | Ootsu |
| 4,557,697 | A * | 12/1985 | Kontar ............... B63B 22/06 114/326 |
| 4,721,055 | A | 1/1988 | Pado |
| 4,727,520 | A | 2/1988 | Tadros |
| 5,046,895 | A | 9/1991 | Baugh |
| 6,158,370 | A | 12/2000 | French et al. |
| 7,496,002 | B2 | 2/2009 | Vosburgh |
| 2014/0348593 | A1* | 11/2014 | Kawahara ............... B66D 1/60 405/224 |

FOREIGN PATENT DOCUMENTS

WO  WO 2001/081169 A1  11/2001
WO  WO 2011/069808 A2  6/2011

* cited by examiner

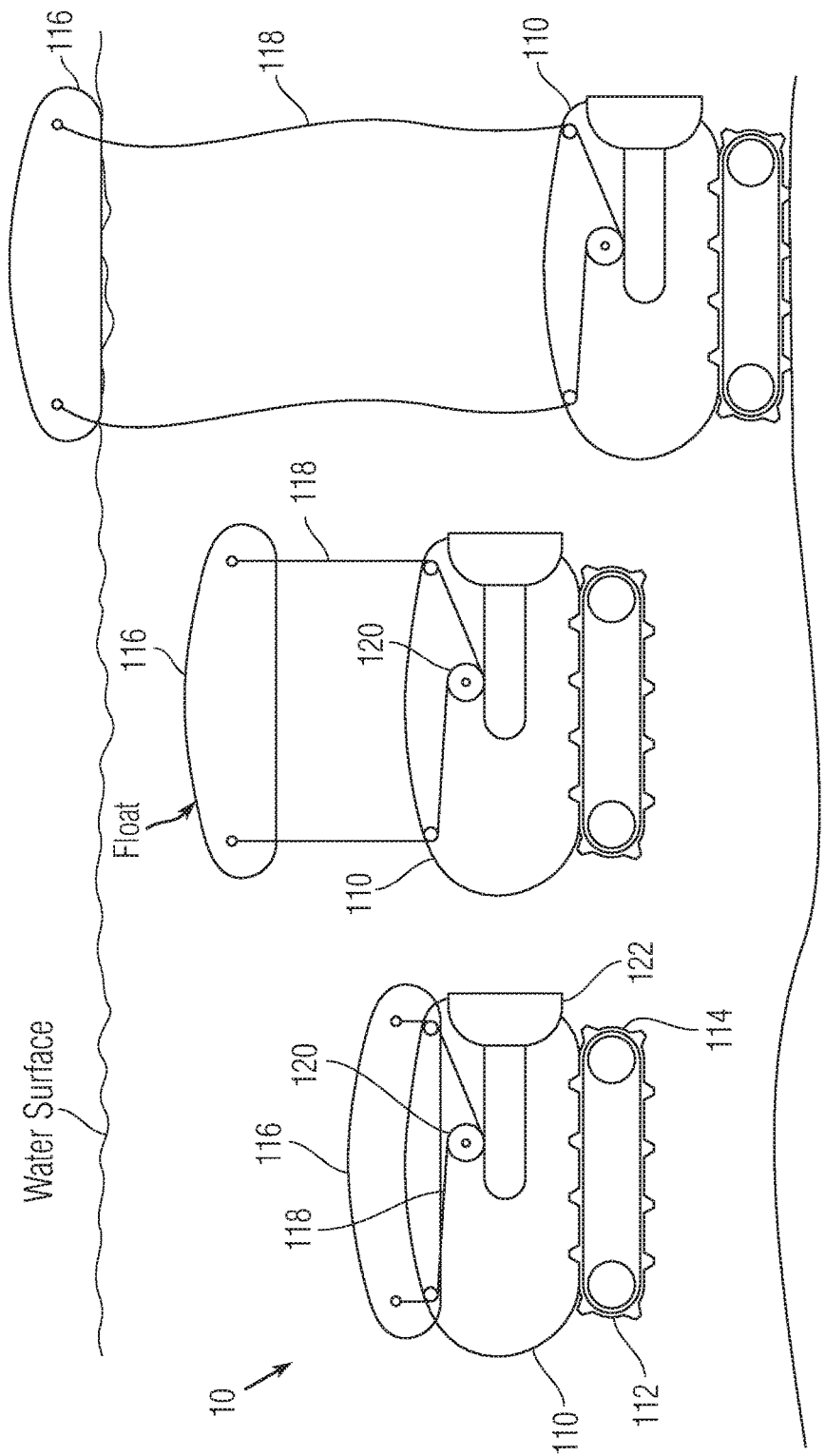

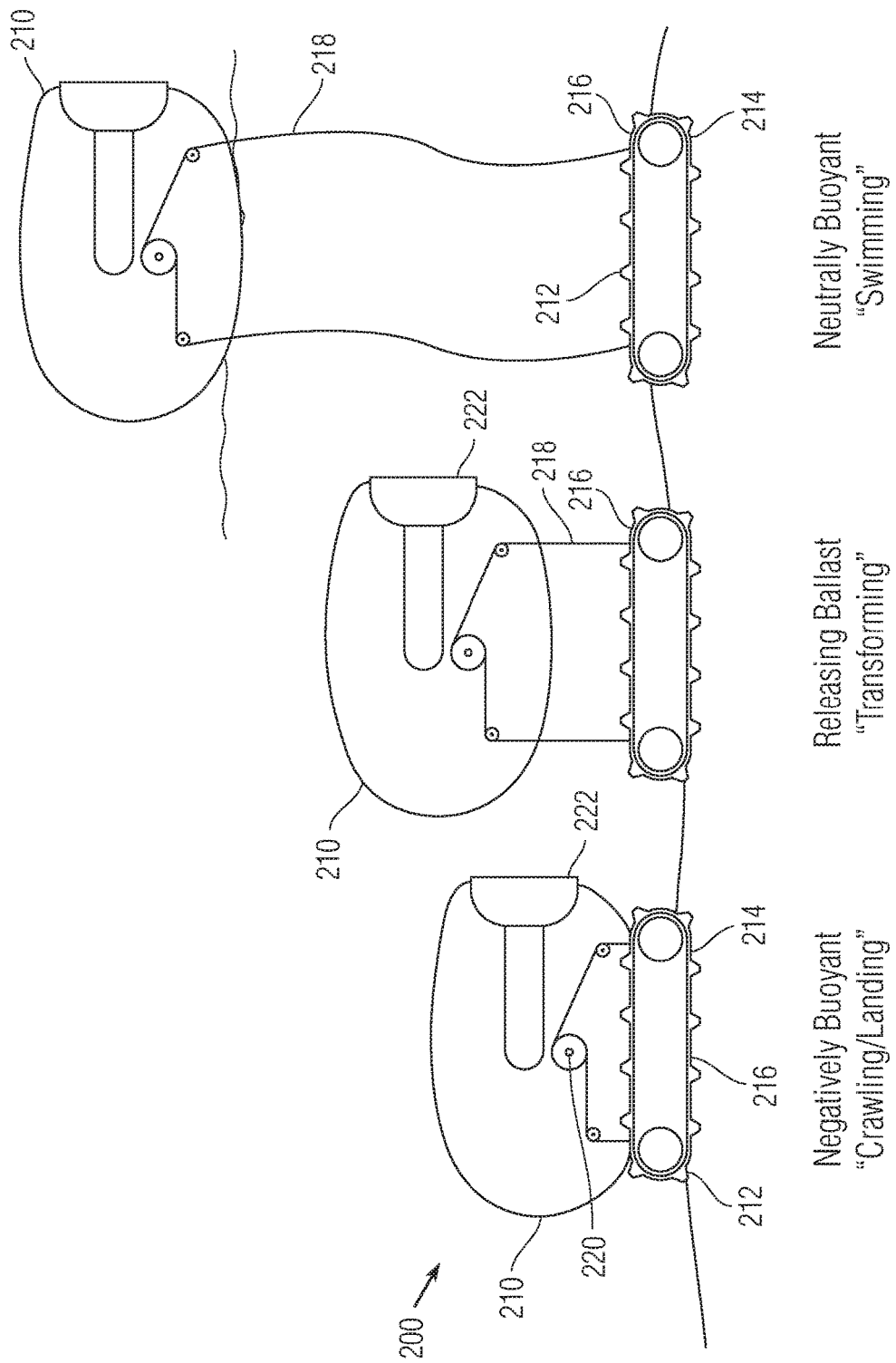

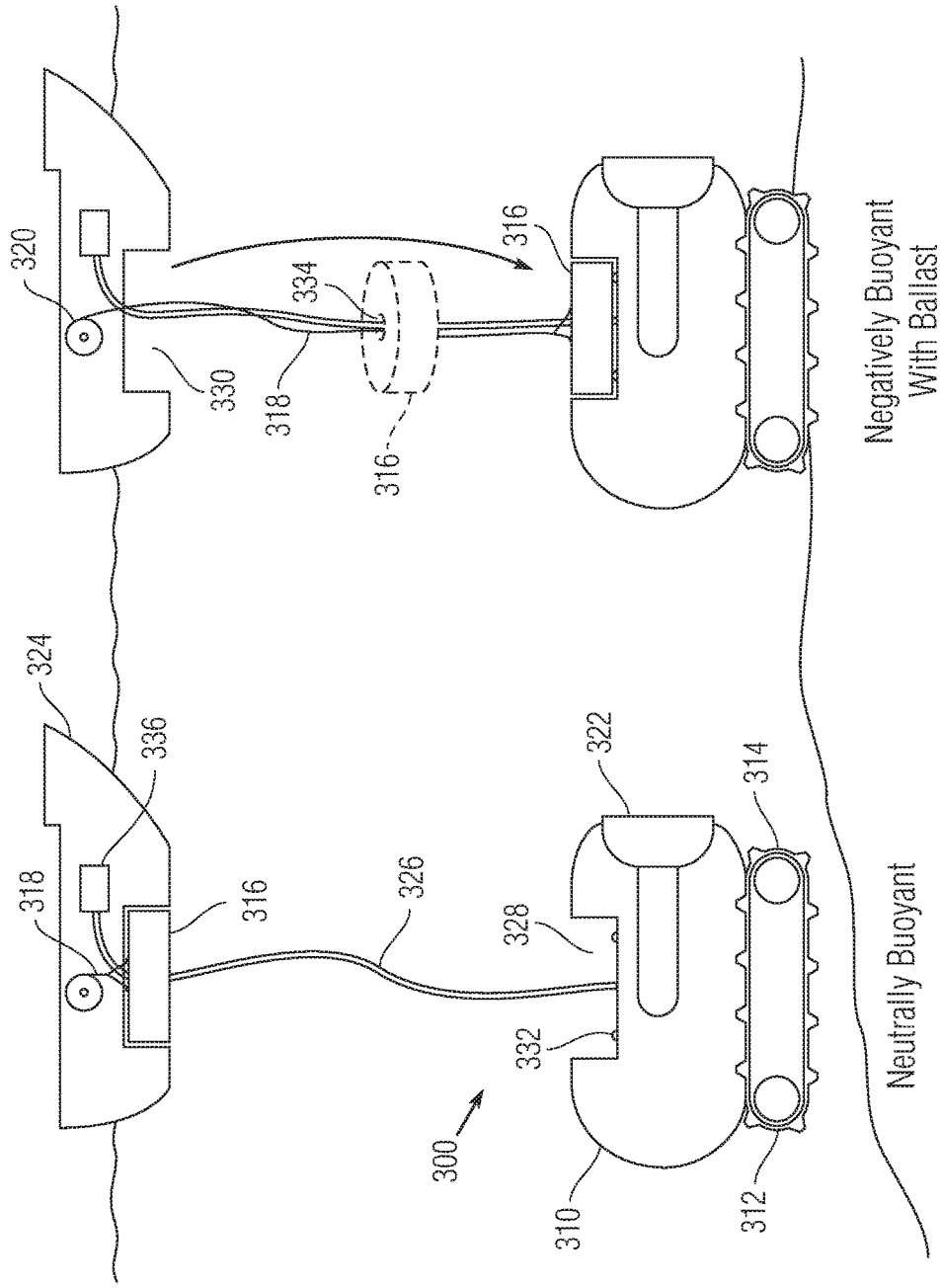

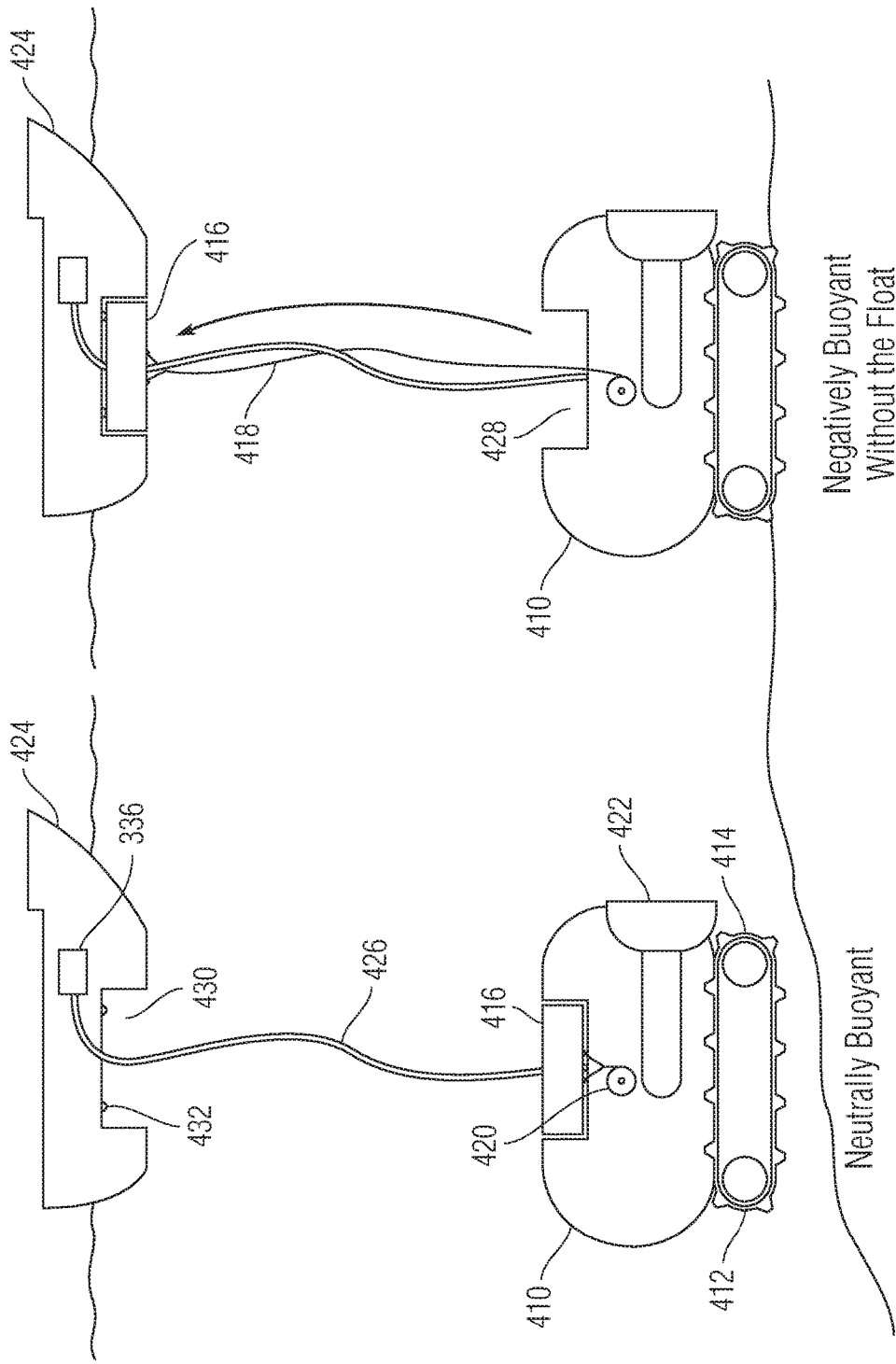

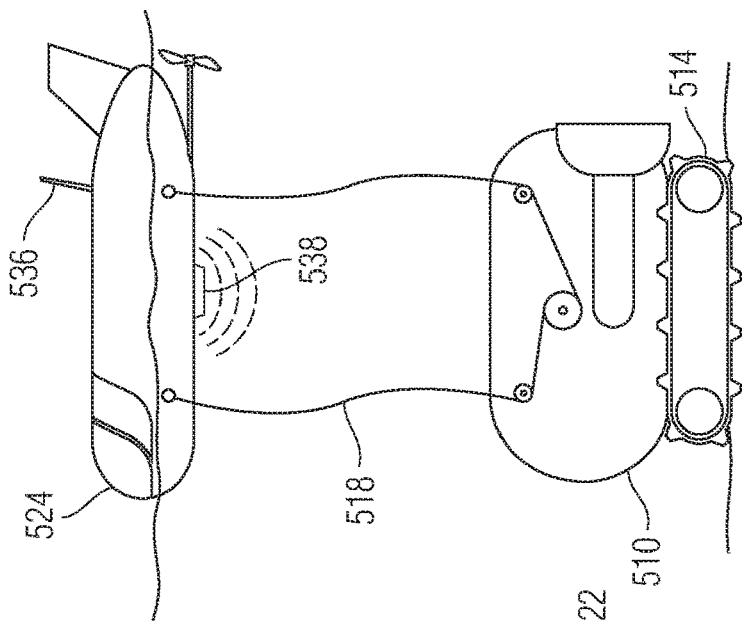
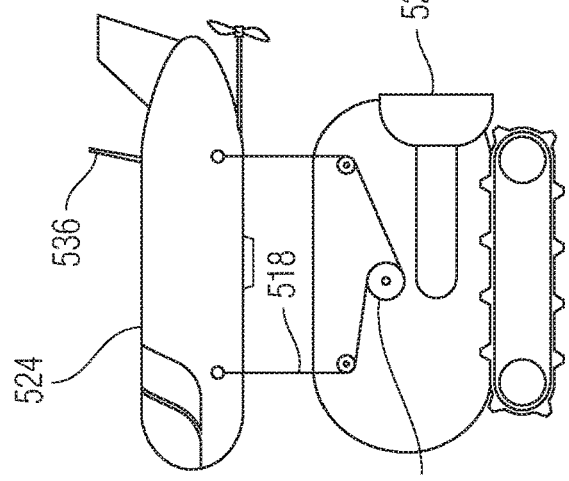
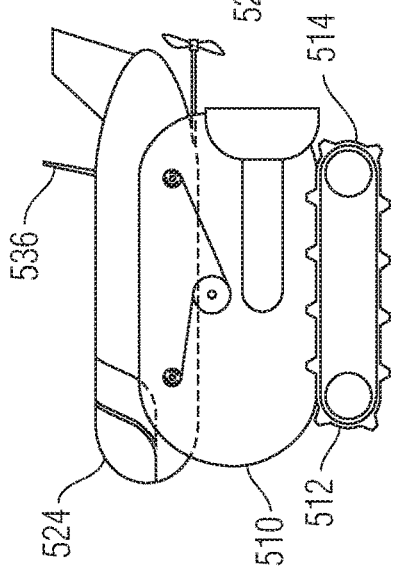
Fig. 5A  Neutrally Buoyant "Swimming" Autonomous/Untethered
Fig. 5B
Fig. 5C  Negatively Buoyant "Crawling/landing" Remote Controlled

REUSABLE BUOYANCY MODULES FOR BUOYANCY CONTROL OF UNDERWATER VEHICLES

CROSS-REFERENCE TO RELATED APPLICATIONS

This application claims priority under 35 U.S.C. § 119 to U.S. Provisional Application Ser. No. 62/397,175, filed Sep. 20, 2016, which is hereby incorporated by reference in its entirety.

FIELD OF THE INVENTION

A system, method, and devices for performing underwater tasks that includes an underwater robot and one or more reusable buoyancy modules.

BACKGROUND OF THE INVENTION

Mobility of underwater vehicles is governed by various factors. A vehicle's density and gravity play a great role in underwater mobility. Underwater vehicles must have the means to counter the effect of their gravity and/or buoyancy in order to swim smoothly through a water column and perform tasks efficiently. An underwater vehicle having a neutrally buoyant state is the optimum condition for swimming and transporting through the water column. In some applications, such as visual inspection of underwater structure or video shooting of underwater target, free swimming with neutral buoyancy is desired. On the other hand, an underwater robot having a negatively buoyant state is desired for crawling or anchoring on the seabed. Some applications, such as fouling cleaning, robotic arm manipulation and maintenance require the underwater vehicle to be stable and heavy on the subsurface floor to overcome the counter effect of operations (i.e., equal and opposite reactionary forces).

The concept of buoyancy control was developed with the earliest evolvement of submarines. Submarines typically change their internal buoyancy by varying their volume underwater using pumps and gas cylinders, i.e., hydraulically. However, hydraulic buoyancy control systems are usually bulky, complicated and optimized for large size, deep underwater vehicles.

Accordingly, there is a need to provide underwater vehicles with a means of controlling buoyancy with an easy to manufacture, operate, and maintain, cost-effective and compact system that can be applied for specific applications and conditions. By utilizing the water surface buoyancy limit and the seabed gravity limit, discrete buoyancy control can be achieved according to the present invention as disclosed herein.

SUMMARY OF THE INVENTION

In one aspect of the invention, a water environment robotic system is provided that includes an underwater robotic vehicle, wherein the underwater robotic vehicle is at least one vehicle of the water environment robotic system. A buoyancy module is configured to be selectively buoyantly engaged and buoyantly disengaged with the underwater robotic vehicle. A tether is connected to the buoyancy module. A motor is operatively connected to the tether and is configured to extend and retract the tether and buoyancy module. In a first condition the tether and buoyancy module are in a retracted position and the underwater robotic vehicle has a first buoyancy. In a second condition the tether and buoyancy module are in an extended position and the underwater robotic vehicle has a second buoyancy. The buoyancy module is in one of the states of being buoyantly engaged or buoyantly disengaged with the underwater robot in the first condition, and the buoyancy module is in the other one of the states of being buoyantly engaged or buoyantly disengaged with the underwater robot in the second condition.

According to a further aspect, the buoyancy module has a positive buoyancy, and in the first condition the buoyancy module is in the retracted position and is buoyantly engaged with the underwater robot causing the first buoyancy of the underwater robot to be higher than the second buoyancy in the second condition in which the buoyance module is in the extended position and is buoyantly disengaged from the underwater robot.

According to a still further aspect, the buoyancy module has a negative buoyancy, and in the first condition the buoyancy module is in the retracted position and is buoyantly disengaged with the underwater robot causing the first buoyancy of the underwater robot to be higher than the second buoyancy in the second condition in which the buoyance module is in the extended position and is buoyantly engaged with the underwater robot.

According to another aspect, the buoyancy module has a neutral buoyancy, and in the first condition the buoyancy module is in the retracted position and is buoyantly engaged with the underwater robot causing the first buoyancy of the underwater robot to be equal to the second buoyancy in the second condition in which the buoyance module is in the extended position and is buoyantly disengaged with the underwater robot.

According to yet another aspect, which can be combined in an embodiment constructed in accordance with one or more of the foregoing aspects, the buoyancy module is incorporated in a surface boat.

According to a further aspect, which can be combined in an embodiment constructed in accordance with one or more of the foregoing aspects, the buoyancy module is a surface boat.

According to a still further aspect, which can be combined in an embodiment constructed in accordance with one or more of the foregoing aspects, the surface boat is configured to perform functions on a surface of the water when the surface boat is in the disengaged condition.

According to a further aspect, wherein tether is in a slack condition the buoyancy module is in the state of being buoyantly disengaged with the underwater robot.

According to another aspect, a robotic system having selectively engageable buoyancy for use in a water environment is provided that includes an underwater robotic vehicle. A buoyancy module that is configured to be selectively engaged and disengaged with the underwater robotic vehicle. A tether is connected to the buoyancy module. A winch is operatively connected to the tether and is configured to extend and retract the tether and buoyancy module. A state controller is connected to the winch and is operative to transition the robotic system between at least two of the following buoyancy states: (1) a first state in which the tether and buoyancy module are in a retracted position and the underwater robotic vehicle has a first buoyancy, and (2) a second state in which the tether and buoyancy module are in an extended position and the underwater robotic vehicle has a second buoyancy. The buoyancy module is either engaged or disengaged with the underwater robot in the first state, and the buoyancy module is in the other one of being engaged or disengaged with the underwater robot in the second condition.

According to yet another aspect, a method for operating a water environment robotic system is provided. The method includes the step of deploying the water environment robotic system into a water environment. The water environment robotic system includes an underwater robotic vehicle, wherein the underwater robotic vehicle is at least one vehicle of the water environment robotic system. The system includes a buoyancy module that is configured to be selectively buoyantly engaged and buoyantly disengaged with the underwater robotic vehicle. A tether is connected to the buoyancy module. A motor is operatively connected to the tether and is configured to extend and retract the tether and buoyancy module. The method includes the step of selectively altering a buoyancy configuration of the water environment robotic system. Selectively altering the buoyancy includes the steps of: extending the tether and buoyancy module; buoyantly disengaging the buoyancy module such that the underwater robotic vehicle has one buoyancy; retracting the tether and buoyancy module; and buoyantly engaging the buoyancy module such that the underwater robotic vehicle has a different buoyancy.

According to a further aspect, the buoyancy module has a positive buoyancy, and in a first condition the buoyancy module is in a retracted position and is buoyantly engaged with the underwater robot causing the buoyancy of the underwater robot to be higher than in a second condition in which the buoyance module is in an extended position and is buoyantly disengaged from the underwater robot.

According to a still further aspect, the buoyancy module has a negative buoyancy, and in a first condition the buoyancy module is in a retracted position and is buoyantly disengaged with the underwater robot causing the buoyancy of the underwater robot to be higher than in a second condition in which the buoyancy module is in an extended position and is buoyantly engaged with the underwater robot.

According to a yet further aspect, the buoyancy module has a neutral buoyancy, and in a first condition the buoyancy module is in a retracted position and is buoyantly engaged with the underwater robot causing the buoyancy of the underwater robot to be equal to the buoyancy in a second condition in which the buoyance module is in the extended position and is buoyantly disengaged with the underwater robot.

According to yet another aspect, which can be combined in an embodiment constructed in accordance with one or more of the foregoing aspects, the buoyancy module is incorporated in a surface boat.

According to a further aspect, which can be combined in an embodiment constructed in accordance with one or more of the foregoing aspects, the buoyancy module is a surface boat.

According to a still further aspect, which can be combined in an embodiment constructed in accordance with one or more of the foregoing aspects, the surface boat is configured to perform functions on a surface of the water when the surface boat is in the disengaged condition.

According to a further aspect, wherein the tether being in a slack condition causes the buoyancy module to be in the state of being buoyantly disengaged with the underwater robot.

BRIEF DESCRIPTION OF THE DRAWINGS

FIGS. 1A-1C show details of the system in accordance with one embodiment of the present invention;

FIGS. 2A-2C show details of the system in accordance with another embodiment of the present invention;

FIGS. 3A-3B show details of the system in accordance with another embodiment of the present invention;

FIGS. 4A-4B show details of the system in accordance with another embodiment of the present invention; and FIGS. 5A-5C show details of the system in accordance with another embodiment of the present invention.

DETAILED DESCRIPTION CERTAIN OF EMBODIMENTS OF THE INVENTION

Referring to FIGS. 1A-1C, an embodiment is illustrated of an aquatic environment robotic system 10 includes an underwater robot 110. The underwater robot 110 can include a lower body portion 112. The main hull of the underwater robot 110 can house various electronics, motors, thrusters, sensors, and power sources, as determined as necessary for a particular operation of the robot. The lower body portion 112 can include tracks 114, as shown in FIG. 1, which can be used to traverse the subsurface floor.

A buoyancy module 116 is connected to the underwater robot 110 via tethers 118 and a motorized pulley or winch system 120. The buoyance module 116 can be connected to the underwater robot 110 via one or more tethers 118. As shown in FIG. 1, the buoyancy module 116 is connected via two tethers 118, one located forward and one located aft. The use of two tethers increases stability and reduces the chances that the underwater robot 110 and the buoyancy module 116 can become misaligned (e.g., the robot flipping with respect to the buoyancy module 116). Moreover, the use of multiple tethers distributes the buoyant force of the buoyancy module 116 over the hull of the underwater robot 110. The tethers 118 are shown connected to a single winch system 120. Alternatively, individual winch systems can be used for each tether.

The winch system 120 includes a motor and a pulley or drum that are configured to extend and retract the tethers 118. The winch system 120 includes a motor and drum or pulley to wind and unwind the tethers 118. For example, when the motor of the winch system 120 rotates in a first direction, the tethers 118 unwind and extend from the underwater robot. When the motor causes of the drum to rotate in opposite direction, the tethers 118 wind onto the drum and retract into the underwater robot. By the mode of operation, the winch system 120 can extend and retract the tethers 118 upon receiving an input control command. A state control device, including among other components a processor configured by code that it executes or otherwise implements and a non-volatile memory, receives and provides commands or an electrical or mechanical user input device, can be connected to the winch to control the operation of the winch, which, in turn, operates to transition the robotic system between at least two buoyancy states, as discussed in more detail below.

As the tethers 118 extend and/or retract by operation of the winch 120, the buoyancy module 116, which is connected to the tethers 118, also extends and retracts, respectively. As discussed in more detail below, this system can be used to engage and disengage the buoyancy module 116 with the underwater robot 110.

FIGS. 1A-1C illustrate the buoyancy module 116 in various states of being engaged and disengaged with the underwater robot 110, which cause the buoyancy of the underwater robot 110 to change as a result of the engaged/disengaged condition of the buoyance module 116. In the particular embodiment shown in FIGS. 1A-1C, the buoyancy module 116 has a positive buoyancy. A positive buoyancy means that the buoyancy module 116 has a density less than the water that the robot is operating in. The positive buoyance of the buoyancy module causes an upward force, i.e., a force toward the top of the water column, to be exerted on the underwater robot.

In FIG. 1A, the tethers 118 are in a retracted position. In other words, the tethers 118 are wound about the drum of the winch system 120 and the buoyancy module 116 is engaged with the underwater robot 110. The buoyancy 116 module is engaged with the underwater robot 110 such that the buoyancy force is transferred through the tethers 118 to the underwater robot. Accordingly, the tethers 118 are under tension and are transmitting that buoyancy force to the underwater robot. In other embodiments, releasable retention clamps (not shown) can be used when the buoyance module 116 is in the fully retracted position and is engaged against the robot 110. Alternatively, the retention clamps can positively engage the buoance module 116 so that the tethers 118 are not under constant, full tension in the full-retracted position.

In FIG. 1B, the winch system 120 is shown in the process of deploying the buoyancy module 116 by extending the tethers 118 so that the buoyancy module is extended away from the underwater robot 110. Due to the positive buoyancy of the buoyancy module 116, the buoyancy module 116 rises through the water column towards the surface of the water. However, the tethers 118 are still under tension and so the buoyancy force is still transferred to the underwater robot 110 through the tethers 118 in configuration shown in FIG. 1B. As such, the buoyancy module 116 is still engaged with the underwater robot 110 in this configuration because the tethers 118 are under tension and exerting force on the underwater robot 110.

In FIG. 1C, the winch system 120 has unwound and has extended sufficient length of the tethers 118 such that the buoyancy module 116 has risen through the water column to the surface of the water and the underwater robot has descended through the water column to make contact with the underwater surface. In this condition, the tethers 118 have been extended to an extent so that the buoyancy force is no longer being transferred through the tethers 118. As shown in FIG. 1C, the buoyancy module 116 is freely floating on the surface of the water and the underwater robot is resting on the undersea surface. The tethers 118 have been extended a length greater than the water column, i.e., greater than the depth of the water in that location, so that the tethers 118 have become slack with respect to the buoyancy module 116 and the underwater robot 110. In this configuration, the buoyance module 116 is disengaged from the robot 110 because the buoyance module is no longer exerting a buoyance force on the robot 110.

In the slack condition illustrated in FIG. 1C, the tethers 118 are no longer transferring the buoyance force to the robot 110. As a result of the tethers 118 no longer transferring the buoyancy force to the underwater robot 110, the net buoyance of the underwater robot 110 has increased. As such, the underwater robot 110 experiences a greater gravitational force which holds it against the undersea surface. The increased net downward force experienced by the underwater robot 110 increases the traction between the underwater robot 110 and the undersea surface. The increased traction allows the robot to travel along the undersea surface in a more stable manner precisely because better traction is maintained. Moreover, this increased traction allows the underwater robot 110 to perform tasks more efficiently because the underwater robot has a greater stability. For example, if the underwater robot 110 were operated to remove fouling from a pipe surface, the force exerted by the fouling removal tool against the pipe would result in an equal and opposite force against the underwater robot 110. As such, there is a tendency for the underwater robot 110 to be pushed away from the pipe as it applies force on the pipe. The increased traction of the underwater robot 110, caused by the reduced buoyancy as a result of the disengagement of the buoyancy module 116, resists this force and allows the robot to stay in the desired position during the cleaning operation.

The mobile robot system 10 can be reconfigured to adjust the buoyancy characteristics of the underwater robot 110 during certain operations and to be adjusted again during other operations, as required. In FIG. 1A, the positive buoyancy of the buoyancy module 116 counteracts the negative buoyancy of the underwater robot 110. In this condition, the engagement between the buoyancy module 116 and the underwater robot 110 results in a neutrally buoyant configuration. A neutrally buoyant configuration is particularly useful for swimming operations of the underwater robot because the system 10 does not have a tendency to move up or down through the water column.

For example, when the robot system 10 is first deployed into the water, it may be desirable to have the buoyancy module 116 engaged with the underwater robot 110, as shown in FIG. 1A. The neutral buoyancy achieved by the engagement of the buoyancy module 116 and the underwater robot 100 improves the efficiency of swimming through the water column and permits the use of thruster 122 to move the robot through the water column. The thrusters 122 can be used to move the robot to a desired position. Once at the desired position, the winch 120 can be activated to extend the tethers 118 to a sufficient extent such that the buoyancy module 116 is floating on the surface of the water and the underwater robot 110 is resting against the subsea surface with sufficient slack in the tethers 118, as shown in FIG. 1C. Once the buoyance module 116 has been disengaged from the underwater robot 110 (i.e., the no force is exerted by the buoyancy module on the underwater robot), the underwater robot 110 has a negatively buoyant condition which is suitable for traversing (i.e., using treads 114 or other means) and operating (performing inspection, cleaning, maintenance operations, etc.) on the undersea surface. After the crawling or other operations conducted on the sea surface are complete, the winch 120 can wind up and retract the tethers, thereby reengaging the buoyance module 116 and the underwater robot 110 (i.e., force is exerted by the buoyancy module on the underwater robot). In this way, after the subsea floor operations are complete the underwater robot is now again neutrally buoyant and can move through the water column in an efficient manner. Once operations are complete, the underwater robot 110 can swim to the surface for retrieval from the water.

Accordingly, in a first condition the underwater robot shown and described in connection with FIGS. 1A-1C can have a first buoyancy, while in a second condition it can have a second buoyancy, and in the third condition it can have third buoyancy. With respect to arrangement shown in FIG. 1, in the first condition the underwater robot has a neutral buoyancy characteristic, in the second condition the underwater robot has a negative buoyancy characteristic, and in the third condition the underwater robot has a neutral buoyancy characteristic. Other arrangements can be constructed in which the various conditions are associated with different buoyancy characteristics than outlined above, as will be appreciated by the skilled reader.

As such, the buoyancy of the underwater robot can be changed using mechanical devices such as winches and tethers. The use of a winch and tether system provides a cost-effective and efficient means of controlling the buoyancy of the vehicle as compared to other systems that require the changing of hydraulic ballast. Moreover, since the buoyancy module remains connected to the underwater vehicle by tethers, the buoyancy module can be recovered and reused after it is disengaged from the underwater robot. This offers significant advantages over typical drop-ballast systems in which ballast material is simply released and disregarded and cannot be reused. Moreover, the ability to engage, disengage, and reengage the buoyancy module permits the buoyance of the robot to be adjusted multiple times throughout an operation. This permits greater flexibility and operation complexity to be achieved with a single launch of the robot. For example, the robot can swim to a first location, land on the seafloor to perform an operation, reengage with the buoyance module so that it can swim to another location, and then land again to perform a second operation. This can be repeated many times before the robot ultimately resurfaces for retrieval from the water. ADD The adjusting of buoyancy by manipulating the ballast modules can be controlled through the use of a number of sensors that can be used to regulate the process to provide a controlled, efficient operation of the system. The underwater robotic vehicle can include an underwater depth sensor, including one of conventional design, to determine the depth of the vehicle under the surface (e.g., the distance between the current position and the surface of the water). A tether sensor can be included to monitor the condition of the tether. For example, the tether sensor can measure a tension/force of the tether (e.g., can comprise a conventional strain gauge). The tether sensor can measure whether the tether is under tension or a slack condition. The tether sensor can be disposed downstream of the winch (i.e., on the tether-deployed side of the winch). A winch encoder can also be provided to measure the number of rotations of the winch and, using this measured data, the length of the unwound (deployed) tether can be determined. For example, these three sensors ("Buoyancy Control Sensors") can be used together to provide the robotic processing unit a feedback on the status of the buoyancy module ("Buoyancy Module Feedback"). For example, by comparing the depth, encoder, and force sensor data signals, the processor, executing software, can determine which status the buoyancy control process is under. For example, if the depth range is higher than the tether encoder length and the tether is under tension, more tether slack is required and the winch could be controlled accordingly. If the tether encoder length is much greater than the depth rating and the tether tension force sensor did not detect tension in the tether for a while, that means that the tether has been slack for some time and retrieving some of it could prevent potential entanglement. A closed loop automatic control could be applied on the buoyancy control system to minimize the effect of drag and the surface waves on the buoyancy status of the underwater robot.

As noted above, the arrangement shown in FIG. 1 incorporates a positively buoyant buoyancy module 116. In addition, negatively buoyant and/or neutrally buoyant buoyancy modules can also be used in other arrangements, as discussed in more detail below. The buoyancy of the buoyancy module can be adjusted by adjusting the density of the material of the buoyancy module and/or adjusting the volume of the buoyancy module. For example, the buoyancy module can be an air filled bladder, or a bladder filled with foam oil or other material that has a density lower than water. A buoyancy module incorporating lower density materials will result in a positively buoyant module. Similarly, a buoyancy module that incorporates denser materials, such as lead weights, sand rocks, or other materials that are denser than water, will result in a negatively buoyant buoyancy module.

FIGS. 2-5 illustrate embodiments that are similar to the embodiment shown in FIG. 1 in that a buoyancy module can be engaged, disengaged, and reengaged to alter the buoyancy of the underwater robot. However, in the various embodiments the combinations of extension/retraction of the buoyancy module and the buoyancy characteristics of the buoyancy module are varied, as discussed in more detail below.

Referring now to FIG. 2, the underwater robot 200 includes an upper portion 210 and a lower portion 212. The upper portion 210 includes a winch system 220 for extending and retracting tethers 218. The lower portion 212 includes tracks 214 that can be used to traverse the sea floor. The lower portion 212 also incorporates a buoyancy module 216. The buoyancy module 216 can be in the form of added weight/ballast that is incorporated into lower portion 212. The buoyancy module 216 can also be integral with the lower portion 212 such that the natural weight of the lower portion 212 also acts as the weight/ballast of the buoyancy module 216. The buoyancy module 216 is negatively buoyant.

In FIG. 2A, the upper portion 210 of the underwater robot 200 is engaged with the lower portion 212, which includes the buoyancy module 216. In this embodiment, the buoyancy module 216 has a negatively buoyant condition. Accordingly, the underwater robot 200 is configured for positive engagement with the seafloor and can travel along the seafloor using tracks 214 and/or perform various operation. In FIG. 2B, the winch system 220 has extended a segment of tether 218 causing the lower body 212 of the underwater robot to extend away from the upper body 210 of the underwater robot. The upper body 210 is neutrally buoyant whereas the lower body 212, which includes the negatively buoyant buoyancy module 216, is negatively buoyant. Accordingly, as the winch 220 extends the tethers 218, the tethers 118 become slack and do not exert a force between the upper body 210 in the lower body 212, as shown in FIG. 2C. In this condition, the buoyance module 216 is disengaged from the upper portion 210 of the underwater robot. The upper portion 210 can be the main portion of the underwater robot and can include the thrusters 222, inspection and maintenance tools, and/or house the main control electronics of the robot. As the buoyance module 216 disengages from the main portion of the underwater robot, the tracks 214 remain on the seafloor. Without the ballast of the buoyancy module 216 being positively engaged, the upper portion 210 is neutrally buoyant and is able to efficiently swim through the water column to perform various operations. The winch system 220 can extend additional length of tether 218 so that the upper body 210 can move a distance from the lower body 212. The tether extending between the upper body 210 and the lower body 212 can be a communication tether that transmits power and/or other signals such as are suitable to transfer data between the upper and lower bodies (e.g., between the underwater swimming robot portion and the tracks 214). For example, the communication tether can comprise insulated electrical conductors. The communication tether can comprise optical wires. The communication tether optionally can include a reinforcement that runs the length to prevent stretching, snapping, shearing or other cutting of a surrounding jacket. In one embodiment, the communication tether can comprise a structured cable including insulated electrical conductors, optical wires, reinforcements, or a combination of these elements, During the configuration shown in FIG. 2C, in which the upper body is neutrally buoyant and able to swim through the water, the tracks 214 on the lower portion 212 can follow the movement of the upper body 210 as it swims through the water column by crawling along the sea floor in a direction the corresponds to the direction of travel of the upper body 210 in order to stay within a maximum separation distance between the upper and lower bodies. In this way, the upper body's travel range is not limited by the length of the tether since the lower body can move to follow the upper body so that the distance between the upper and lower bodies does not exceed the length of the tether. Accordingly, the area of operation of the robot can be expanded by providing a mobile platform. Data signals concerning the movement of the upper body can be transmitted (e.g., through the tether) to the lower body in order to determine appropriate, corresponding movements and/or the upper body can transmit drive command signals directly to the lower body to control its movements so that it moves in a complimentary manner.

In FIG. 2A, the underwater robot has a crawling configuration and is suited for crawling on the undersea surface due to its negatively buoyant characteristic. In FIG. 2C, the upper body 210 is disengaged from the lower body 212, and the upper body is free to swim through the water column due to its neutrally buoyant characteristic while the lower body remains resting on the seafloor due to its negatively buoyant characteristic. After the swimming operation is performed, the winch can retract the tethers to reengage the upper portion and the lower portion (including the buoyancy module) so that the robot can traverse the seafloor and move to the next location. The robotic system shown in FIGS. 2A-2C can include Buoyancy Control Sensors and Buoyancy Module Feedback processing as similarly discussed above. The Buoyancy Control Sensors can include an altimeter sensor, a tether force sensors, and a winch encoder. The upper body can include the altimeter sensor in order to determine the distance between the upper body and the seafloor. Data from the three sensors can be used to provide signals to the robot processing unit which comprises feedback concerning the status of the buoyancy module. For example, by comparing the altitude, encoder and force sensors readings, the processor can determine the present status of the buoyancy control process (e.g., negatively buoyant, transitioning, or neutrally buoyant). As one operation example, if the outcome of the altitude measurement is higher than a current tether encoder length stored in a memory and the tether is under tension, as known from a tether sensor, then more tether slack is required and the winch can be controlled accordingly to winch out an additional length of tether. If the current tether encoder length stored in the memory is much greater than the altitude reading and the tether tension force sensor does not detect tension in the tether for an extended period of time, this condition likely indicates that the tether has been slack for a significant period and retrieving some tether (e.g., by controlling the winch to reel in) can reduce the chance of tether entanglement. A closed loop automatic control can further be applied on the buoyancy control system to minimize the effect of drag and the surface waves on the buoyancy status of the robot.

Referring now to FIG. 3, the underwater robotic system 300 includes an underwater robot 310 and a surface vehicle 324. The surface vehicle 324 and the underwater robot 310 can be connected by via a vehicle tether 326. The vehicle tether 326 can be a communication tether that can transmit power and/or electrical signals (e.g., from electronics box 336) for transferring data and other information between the surface vehicle 324 and the underwater robot 310. The surface vehicle 324 can be a support boat for the underwater robot 310. The surface vehicle 324 can remain on the surface of the water at the top of the water column and the underwater robot 310 can swim through the water column and/or land on the subsurface floor to perform various tasks. The underwater robot 310 can include a thruster 322 for propulsion through the water column and lower portion 312 that includes tracks 314 for traversing the subsurface floor.

The surface vehicle 324 includes a winch system 320 that can be used to wind and unwind a tether 318 that is connected to a buoyance module 316. Referring to FIG. 3A, the tether 118 and buoyancy module 316 are in a retracted condition and the buoyancy module 316 is disengaged from the underwater robot 310. As can be seen, when the tether 318 is retracted, the buoyancy module 316 is adjacent the surface vehicle 324. In this condition, in which the buoyancy module 316 is disengaged from the underwater robot 310, the underwater robot 310 is neutrally buoyant. Accordingly, the underwater robot 310 can efficiently swim through the water column using thrusters 322.

In FIG. 3B, the winch system 320 has been commanded and operated to unwind and extend the tether 318. As the tether 318 and buoyancy module 316 extend, the buoyancy module 316 engages with the underwater robot 310. The buoyancy module 316 has a negatively buoyant characteristic. Accordingly, when the buoyancy module 316 is lowered from the surface boat 324 to engage with the underwater robot 310, the buoyancy of the underwater robot decreases by an amount equal to the negative buoyancy of the buoyancy module and the underwater robot becomes negatively buoyant. The underwater robot 310 can include a recess 328 for receiving the buoyancy module 316 when in the extended and engaged condition. Similarly, the surface boat 324 can include a recess 330 for receiving the buoyancy module 316 when in the retracted and disengaged condition. The buoyancy module 316 and/or underwater robot 310 can include a latching mechanism (e.g., magnets 332) that securely engage the buoyancy module 316 to the underwater robot 310. The secure engagement provided by the magnets can prevent inadvertent disengagement between the buoyancy module 316 and the underwater robot 310, for example, as the underwater robot goes over bumps or uneven surfaces on the seafloor. The buoyancy module 316 can be ring shaped having a central aperture 334 that is sized and shaped to receive the vehicle tether 326. The buoyancy module 316 can comprise multiple, discrete units that can be deployed individually and/or in groups so that the buoyancy can be controlled incrementally by independent control of each buoyancy module. The latching mechanisms facilitate the release/engagement of single and/or multiple buoyancy modules by engaging and disengaging buoyancy modules to the underwater robot 310. The central aperture 334 can have a smooth, conically shaped profile that reduces potentially chaffing as the buoyancy module slides along the vehicle tether 326. The central aperture 334 can also include rollers to facilitate movement along the vehicle tether 326 and reduce chaffing or other potential damage. Similarly, as discussed above, the robotic system can include Buoyancy Control Sensors and Buoyancy Module Feedback processing in which depth/altimeter sensors, winch encoders, and tether tension sensors can be used to efficiently and smoothly control the buoyancy adjustment operations.

Referring to FIG. 4, the underwater robotic system includes a surface vehicle 424 and an underwater robot 410 connected via a vehicle tether 426. The system shown in FIG. 4 is similar to the system shown in FIG. 3, with the major differences being that the buoyancy module 416 has a positive buoyancy and the winch system 420 is supported by the underwater robot 410 to extend and retract the buoyancy module 416. Accordingly, similar parts share a similar numbering convention, except that a "4" prefix is used instead of a "3" prefix.

As shown in FIG. 4A, the tether 418 is wound about the drum of the winch 420. The buoyancy module 416 is a retracted position and is engaged with the underwater robot 410. In this configuration, the buoyancy module 416 exerts a positively buoyant force on the underwater robot 410 causing the underwater robot to be neutrally buoyant.

In FIG. 4B, the winch has been operated to extent the tether 418 causing the buoyancy module 416 to extend away and disengage from the underwater robot 410. As shown, the buoyancy module 416 is received by the surface vehicle 424. The tether 418 is slack and no force is exerted by the buoyancy module 416 on the underwater robot 410. The disengagement of the positively buoyant buoyancy module 416 from the underwater robot 410 reduces the net buoyancy of the underwater robot 410. Accordingly, the underwater robot 410 becomes negatively buoyant and is better suited for traversing the seafloor.

In both the arrangement shown in FIGS. 3 and 4, the vehicle tether is sufficiently long so that the vehicle tether does not exert a buoyancy force on the underwater robot due to the buoyancy of the surface vehicle and/or the buoyancy module. Accordingly, when the buoyancy module is in the extended position, the buoyancy of the surface vehicle does not inadvertently affect the buoyancy of the underwater robot. As such, in the extended position the tethers connected to the buoyancy modules are no longer under tension and do not transfer a buoyancy force. As discussed above, in a similar fashion, the robotic system can include Buoyancy Control Sensors and Buoyancy Module Feedback processing in which depth/altimeter sensors, winch encoders, and tether tension sensors can be used to efficiently and smoothly control the buoyancy adjustment operations.

Referring to FIG. 5, the underwater robotic system 500 includes an underwater robot 510 and a surface vehicle 524. The system shown in FIG. 5 is similar to the systems shown in FIGS. 3 and 4, with the major differences being that the surface vehicle 524 is a hybrid vehicle that can both travel underwater and on the water surface and that the buoyancy module 516 is incorporated into the surface vehicle 524. Accordingly, similar parts share a similar numbering convention, except that a "5" prefix is used instead of a "3" or "4" prefix.

Referring FIG. 5A, the surface vehicle 524 and the underwater robot 510 are engaged and the two vehicles have a neutral net buoyancy. As shown in FIG. 5B, the winch system 520 has operated to extend the tethers 518 so that the surface vehicle 524 and the underwater robot are partially extended away from each other. However, in the configuration shown in FIG. 5B, the surface vehicle is still in the water column and has not yet reached the surface. As such, the tethers 518 are still under tension and so the buoyancy module 516, which is incorporated into the surface vehicle 524, exerts a buoyancy force on the underwater robot 510. The buoyancy module 516 can be in the form of added positively buoyant material that is incorporated into surface vehicle 524. The buoyance module 516 can also be integral with the surface vehicle 524 such that the natural buoyance of the lower portion surface vehicle 524 also provides the positive buoyancy of the buoyancy module 516.

In FIG. 5C, the winch 520 has extended a sufficient length of tether 518 so that the surface vehicle 524 has reached the surface of the water at the top of the water column and the tethers 518 are slack. In the extended, slack condition, the tethers 518 do not transmit force from the buoyancy module 516 to the underwater robot 510 and so the buoyancy module 516 and the underwater robot 510 are disengaged. In this condition, the underwater robot 510 is negatively buoyant and lands on the subsurface floor where it is suitable for traversing the floor and performing various tasks.

The surface vehicle 524 can also include communication relay 536 that can receive communications over the air from a remote control station and then relay those signals to the underwater robot 510, either wirelessly through the water or through a communication tether (not shown). The surface vehicle 524 can also include a position sensor 538 for tracking the relative position of the underwater robot 510 to the surface vehicle 524. The surface vehicle 524 can also include processors for calculating the relative position of the two vehicles and can further include a propulsion system 540 that can be commanded to move the surface vehicle 524 so that a relative positioning is maintained between the underwater robot 510 and the surface vehicle 524 as the underwater robot performs its various operations. Again, similarly, the robotic system can include Buoyancy Control Sensors and Buoyancy Module Feedback processing in which depth/altimeter sensors, winch encoders, and tether tension sensors can be used to efficiently and smoothly control the buoyancy adjustment operations, as discussed above. Further, as similarly discussed above, the surface vehicle can be controlled to move in a corresponding manner to follow the movements of the underwater robot.

As discussed above, the various embodiments of the present invention provide significant advantage in operating in a water environment by providing a robotic system that can perform various tasks that require differing buoyancy characteristics, by using the same vehicle without having to retrofit or modify the vehicle offline in a time-consuming, costly operation. The buoyancy of the underwater robot can be changed using mechanical devices such as winches and tethers during the operation of the robot, after it has been deployed into the water. The use of a winch and tether system provides a cost-effective and efficient means of controlling the buoyancy of the vehicle as compared to other systems that require the changing of hydraulic ballast. Moreover, since the buoyancy module remains connected to the underwater vehicle by tethers, the buoyancy module can be recovered and reused after it is disengaged from the underwater robot. This offers significant advantages over typical drop-ballast systems in which ballast material is simply released and disregarded and cannot be reused. Moreover, the ability to engage, disengage, and reengage the buoyancy module permits the buoyance of the robot to be adjusted multiple times throughout an operation, thereby increasing the versatility of the robot while reducing the need to have separate robots for performing different tasks and/or retrieving the robot mid-operation to manually change its buoyancy characteristics.

It should be understood that like numerals in the drawings represent like elements through the several figures, and that not all components and/or steps described and illustrated with reference to the figures are required for all embodiments or arrangements. It should also be understood that the embodiments, implementations, and/or arrangements of the systems and methods disclosed herein can be incorporated as a software algorithm, application, program, module, or code residing in hardware, firmware and/or on a computer useable medium (including software modules and browser plug-ins) that can be executed in a processor of a computer system or a computing device to configure the processor and/or other elements to perform the functions and/or operations described herein. It should be appreciated that according to at least one embodiment, one or more computer programs, modules, and/or applications that when executed perform methods of the present disclosure need not reside on a single computer or processor, but can be distributed in a modular fashion amongst a number of different computers or processors to implement various aspects of the systems and methods disclosed herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The subject matter described above is provided by way of illustration only and should not be construed as limiting. Various modifications and changes can be made to the subject matter described herein without following the example embodiments and applications illustrated and described, and without departing from the true spirit and scope of the present invention, which is set forth in the following claims.

Notably, the figures and examples above are not meant to limit the scope of the present application to a single implementation, as other implementations are possible by way of interchange of some or all of the described or illustrated elements. Moreover, where certain elements of the present application can be partially or fully implemented using known components, only those portions of such known components that are necessary for an understanding of the present application are described, and detailed descriptions of other portions of such known components are omitted so as not to obscure the application. In the present specification, an implementation showing a singular component should not necessarily be limited to other implementations including a plurality of the same component, and vice-versa, unless explicitly stated otherwise herein. Moreover, applicants do not intend for any term in the specification or claims to be ascribed an uncommon or special meaning unless explicitly set forth as such. Further, the present application encompasses present and future known equivalents to the known components referred to herein by way of illustration.

The foregoing description of the specific implementations will so fully reveal the general nature of the application that others can, by applying knowledge within the skill of the relevant art(s) (including the contents of the documents cited and incorporated by reference herein), readily modify and/or adapt for various applications such specific implementations, without undue experimentation, without departing from the general concept of the present application. Such adaptations and modifications are therefore intended to be within the meaning and range of equivalents of the disclosed implementations, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s). It is to be understood that dimensions discussed or shown are drawings are shown accordingly to one example and other dimensions can be used without departing from the invention.

While various implementations of the present application have been described above, it should be understood that they have been presented by way of example, and not limitation. It would be apparent to one skilled in the relevant art(s) that various changes in form and detail could be made therein without departing from the spirit and scope of the application. Thus, the present application should not be limited by any of the above-described example implementations.

The invention claimed is:

1. A water environment robotic system, comprising:
an underwater robotic vehicle, wherein the underwater robotic vehicle is at least one vehicle of the water environment robotic system;
a surface boat incorporating or comprising a buoyancy module that is configured to be selectively buoyantly engaged and buoyantly disengaged with the underwater robotic vehicle;
a tether connected to the buoyancy module; and
a motor operatively connected to the tether and being configured to extend and retract the tether and buoyancy module;
wherein in a first condition the tether and buoyancy module are in a retracted position and the underwater robotic vehicle has a first buoyancy, and in a second condition the tether and buoyancy module are in an extended position and the underwater robotic vehicle has a second buoyancy,
wherein the buoyancy module is in one of the states of being buoyantly engaged or buoyantly disengaged with the underwater robot in the first condition, and the buoyancy module is in the other one of the states of being buoyantly engaged or buoyantly disengaged with the underwater robot in the second condition.

2. The water environment robotic system of claim 1, wherein the buoyancy module has a positive buoyancy, and in the first condition the buoyancy module is in the retracted position and is buoyantly engaged with the underwater robot causing the first buoyancy of the underwater robot to be higher than the second buoyancy in the second condition in which the buoyance module is in the extended position and is buoyantly disengaged from the underwater robot.

3. The water environment robotic system of claim 1, wherein the buoyancy module has a negative buoyancy, and in the first condition the buoyancy module is in the retracted position and is buoyantly disengaged with the underwater robot causing the first buoyancy of the underwater robot to be higher than the second buoyancy in the second condition in which the buoyance module is in the extended position and is buoyantly engaged with the underwater robot.

4. The water environment robotic system of claim 1, wherein the buoyancy module has a neutral buoyancy, and in the first condition the buoyancy module is in the retracted position and is buoyantly engaged with the underwater robot causing the first buoyancy of the underwater robot to be equal to the second buoyancy in the second condition in which the buoyance module is in the extended position and is buoyantly disengaged with the underwater robot.

5. The water environment robotic system of claim 1, wherein the surface boat is configured to perform functions on a surface of the water when the surface boat is in the disengaged condition.

6. The water environment robotic system of claim 1, wherein the tether being in a slack condition causes the buoyancy module to be in the state of being buoyantly disengaged with the underwater robot.

7. A method for operating a water environment robotic system, comprising the steps of:
  deploying the water environment robotic system into a water environment, the water environment robotic system comprising:
    an underwater robotic vehicle, wherein the underwater robotic vehicle is at least one vehicle of the water environment robotic system;
    a buoyancy module that is configured to be selectively buoyantly engaged and buoyantly disengaged with the underwater robotic vehicle;
    a tether connected to the buoyancy module; and
    a motor operatively connected to the tether and being configured to extend and retract the tether and buoyancy module;
  selectively altering a buoyancy configuration of the water environment robotic system, comprising the steps of:
    extending the tether and buoyancy module;
    buoyantly disengaging the buoyancy module such that the underwater robotic vehicle has one buoyancy;
    retracting the tether and buoyancy module; and
    buoyantly engaging the buoyancy module such that the underwater robotic vehicle has a different buoyancy,
  wherein the tether being in a slack condition causes the buoyancy module to be in the state of being buoyantly disengaged with the underwater robot.

8. The method of claim 7, wherein the water environment robotic system is deployed with a buoyancy module which has a positive buoyancy, and in a first condition the buoyancy module is in a retracted position and is buoyantly engaged with the underwater robot causing the buoyancy of the underwater robot to be higher than in a second condition in which the buoyance module is in an extended position and is buoyantly disengaged from the underwater robot.

9. The method of claim 7, wherein the water environment robotic system is deployed with a buoyancy module which has a negative buoyancy, and in a first condition the buoyancy module is in a retracted position and is buoyantly disengaged with the underwater robot causing the buoyancy of the underwater robot to be higher than in a second condition in which the buoyance module is in an extended position and is buoyantly engaged with the underwater robot.

10. The method of claim 7, wherein the water environment robotic system is deployed with a buoyancy module which has a neutral buoyancy, and in a first condition the buoyancy module is in a retracted position and is buoyantly engaged with the underwater robot causing the buoyancy of the underwater robot to be equal to the buoyancy in a second condition in which the buoyance module is in the extended position and is buoyantly disengaged with the underwater robot.

11. The method of claim 7, further comprising the step of including the buoyancy module in a surface boat before the step of deploying the water environment robotic system.

12. The water environment robotic system of claim 1, wherein the surface boat is configured to perform functions on a surface of the water when the surface boat is in the disengaged condition.

* * * * *